US00PP36092P3

(12) United States Plant Patent
Pieters

(10) Patent No.: US PP36,092 P3
(45) Date of Patent: Sep. 3, 2024

(54) ***CHRYSANTHEMUM* PLANT NAMED 'JOSARARBR'**

(50) Latin Name: ***Chrysanthemum* X *morifolium***
Varietal Denomination: Josararbr

(71) Applicant: PIETERS JOSEPH & LUC B.V., Staden-Oostnieuwkerke (BE)

(72) Inventor: Christophe Pieters, Staden-Oostnieuwkerke (BE)

(73) Assignee: PIETERS JOSEPH + LUC B.V., Staden-Oostnieuwkerke (BE)

( * ) Notice: Subject to any disclaimer, the term of this patent is extended or adjusted under 35 U.S.C. 154(b) by 0 days.

(21) Appl. No.: 18/527,282

(22) Filed: Dec. 2, 2023

(65) Prior Publication Data

US 2024/0188463 P1 Jun. 6, 2024

Related U.S. Application Data

(60) Provisional application No. 63/430,011, filed on Dec. 3, 2022.

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ..... A01H 6/1424; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Chrysanthemum* plant named 'Josararbr', characterized by its relatively compact, upright, outwardly spreading and uniformly rounded plant habit; vigorous growth habit; freely branching habit; dense and full plant habit; medium green-colored leaves; early, uniform and freely flowering habit; decorative type inflorescences with ray florets that are reddish bronze in color; relative resistance to Fusarium Wilt, White Rust and Verticillium Wilt; and good greenhouse and outdoor performance.

2 Drawing Sheets

Figure 1:
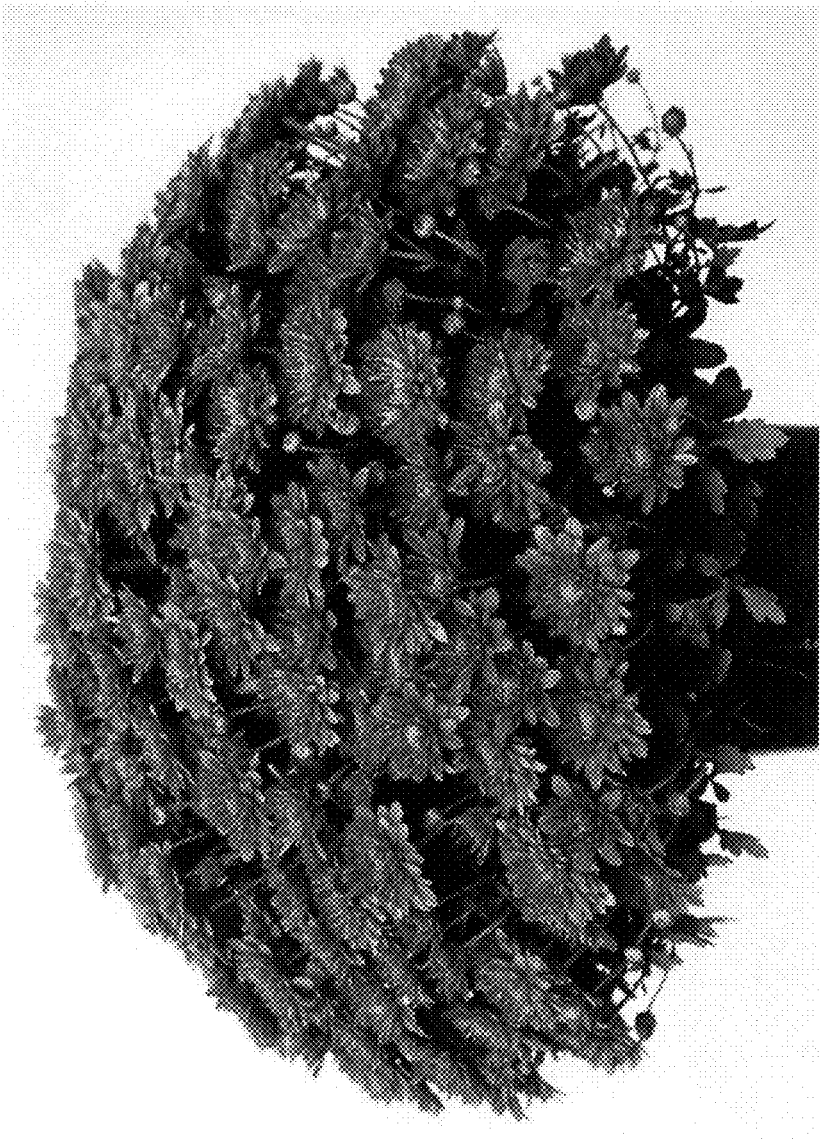

Botanical designation: *Chrysanthemum* X *morifolium*.
Cultivar denomination: 'JOSARARBR'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Pieters Joseph & Luc B.V. of Staden-Oostnieuwkerke, Belgium on Jan. 17, 2022, application number 2022/0151. Foreign priority is not claimed to this European Community Plant Breeder's Rights application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* X *morifolium* and hereinafter referred to by the name 'Josararbr'.

The new *Chrysanthemum* plant is a product of a planned breeding program conducted by the Inventor in Staden-Oostnieuwkerke, Belgium. The objective of the breeding program is to create new uniformly mounding and freely flowering *Chrysanthemum* plants with unique and attractive ray floret coloration.

The new *Chrysanthemum* plant is a naturally-occurring whole plant mutation of *Chrysanthemum* X *morifolium* 'Josarama', disclosed in U.S. Plant patent application Ser. No. 18/527,274. 'Josarama' was originally referred to as 'Josarma' in the provisional U.S. Patent Application. The new *Chrysanthemum* plant was discovered and selected by the Inventor as a single flowering plant from within a population of plants of 'Josarama' in a controlled greenhouse environment in Staden-Oostnieuwkerke, Belgium in October, 2017.

Asexual reproduction of the new *Chrysanthemum* plant by vegetative terminal cuttings was first conducted in a controlled greenhouse environment in Staden-Oostnieuwkerke, Belgium in February, 2018. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Josararbr'. These characteristics in combination distinguish 'Josararbr' as a new and distinct *Chrysanthemum* plant:

1. Relatively compact, upright, outwardly spreading and uniformly rounded plant habit.
2. Vigorous growth habit.
3. Freely branching habit; dense and full plant habit.
4. Medium green-colored leaves.
5. Early, uniform and freely flowering habit.
6. Decorative type inflorescences with ray florets that are reddish bronze in color.
7. Relative resistant to Fusarium Wilt, White Rust and Verticillium Wilt.
8. Good greenhouse and outdoor performance.

Plants of the new *Chrysanthemum* can be compared to plants of the mutation parent, 'Josarama'. In side-by-side comparisons, plants of the new *Chrysanthemum* differ primarily from plants of 'Josarama' in ray floret color as ray florets of plants of the new *Chrysanthemum* are reddish bronze in color whereas ray florets of plants of 'Josarama' are dark purplish red in color.

Plants of the new *Chrysanthemum* can be compared to plants of *Chrysanthemum* X *morifolium* 'JO44ORA', not patented. In side-by-side comparisons, plants of the new *Chrysanthemum* differ primarily from plants of 'JO44ORA' in the following characteristics:

1. Plants of the new *Chrysanthemum* are more compact than plants of 'JO44ORA'.
2. Inflorescences of plants of the new *Chrysanthemum* have more ray florets and are denser than inflorescences of 'JO44ORA'.
3. Ray florets of plants of the new *Chrysanthemum* are reddish bronze in color whereas ray florets of plants of 'JO44ORA' are orangish bronze in color.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering plant of 'Josararbr' grown in a container.

Figure 2:
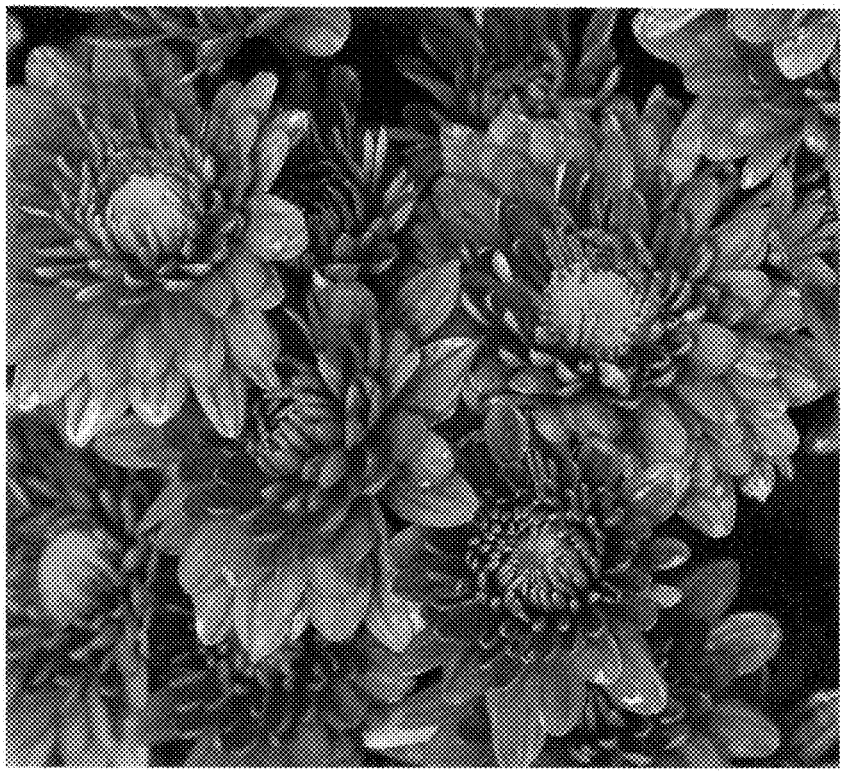

The photograph on the second sheet (FIG. 2) is a close-up view of a typical flowering plant of 'Josararbr'.

DETAILED BOTANICAL DESCRIPTION

The aforementioned photographs and following observations and measurements describe plants grown in 19-cm containers in an outdoor nursery in Staden-Oostnieuwkerke, Belgium under natural daylengths during the autumn and employing cultural practices typically used in commercial *Chrysanthemum* production. During the production of the plants, day temperatures ranged from 10 C to 25 C and night temperatures ranged from 5 C to 15 C. Plants were 3.5 months old when the photographs and detailed description were taken. In the following description, color references are made to The Royal Horticultural Society Colour Chart, 2015 Edition, except where general terms of ordinary dictionary significance are used.

Botanical classification: *Chrysanthemum* X *morifolium* 'Josararbr'.

Parentage: Naturally-occurring whole plant mutation of *Chrysanthemum* X *morifolium* 'Josarama', disclosed in U.S. Plant patent application Ser. No. 18/527,274.

Propagation:

*Type cutting*.—By vegetative tip cuttings.

*Time to initiate roots, summer*.—About 14 days at temperatures about 20 C.

*Time to initiate roots, winter*.—About 20 days at temperatures about 20 C.

*Time to produce a rooted young plant, summer*.—About three weeks at temperatures about 20 C.

*Time to produce a rooted young plant, winter*.—About four weeks at temperatures about 20 C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Appearance*.—Perennial decorative type *Chrysanthemum*; plants relatively compact, upright to outwardly spreading giving a uniformly rounded appearance to the plant; plants roughly spherical and flattened globular in overall shape; very freely branching habit with about 16 primary lateral branches, each primary lateral branch with about seven secondary branches; pinching is not required, but will enhance lateral branch development; dense and full plant habit; vigorous growth habit and rapid growth rate; plants flexible, not brittle.

*Plant height, soil level to top of foliar plane*.—About 28 cm.

*Plant height, soil level to top of floral plane*.—About 31.8 cm.

*Plant width*.—About 51.5 cm.

*Lateral branches*.—Length: About 12.5 cm. Diameter: About 4 mm. Internode length: About 1.4 cm. Strength: Strong. Aspect: Erect to about 25 degrees from vertical. Texture and luster: Densely pubescent; slightly glossy. Color, developing: Close to 143C. Color, developed: Close to 143A to 143B; longitudinal ridges, close to 197A.

*Leaves*.—Arrangement: Alternate, simple. Length: About 4.4 cm. Width: About 3.1 cm. Shape in overall outline: Obovate to broadly elliptic. Apex: Abruptly acute. Base: Long attenuate. Margin: Palmately lobed and coarsely dentate-serrate, sinuses between lateral lobes divergent and medium in depth. Texture and luster, upper surface: Moderately pubescent; matte to slightly glossy. Texture and luster, lower surface: Densely pubescent; matte to slightly glossy. Venation: Palmately reticulate. Color: Developing leaves, upper surface: Close to a blend of 137B and 143A. Developing leaves, lower surface: Close to 138B. Fully expanded leaves, upper surface: Close to NN137B; venation, close to 138B. Fully expanded leaves, lower surface: Close to 147B; venation, close to 148B. Petioles: Length: About 5 mm. Diameter: About 1.5 mm to 2.5 mm. Strength: Moderately strong. Texture and luster, upper and lower surfaces: Densely pubescent; moderately glossy. Color, upper surface: Close to 146B. Color, lower surface: Close to 148B; at the marginal edges, close to 147B. Stipules: Length: About 5 mm. Diameter: About 3 mm. Shape: Broadly oblong. Apex: Abruptly acute. Base: Broadly cuneate. Texture and luster, upper surface: Moderately pubescent; matte to slightly glossy. Texture and luster, lower surface: Densely pubescent; matte to slightly glossy. Color, upper surface: Close to NN137B. Color, lower surface: Close to 147B.

Inflorescence description:

*Appearance*.—Decorative type inflorescence form; inflorescences borne on terminals above foliar plane; disc and ray florets arranged acropetally on a capitulum.

*Fragrance*.—Moderately fragrant, pungent.

*Flowering response*.—Early and long flowering time; under natural season conditions, plants flower during the autumn into the winter in Belgium; flowering response time, about 45 days.

*Postproduction longevity*.—Inflorescences maintain good color and substance for about two weeks; inflorescences persistent.

*Quantity of inflorescences*.—About twelve inflorescences per lateral branch and about 1,350 inflorescences develop per plant.

*Inflorescence buds*.—Height: About 9 mm. Diameter: About 9.5 mm. Shape: Flattened globular. Texture and luster: Smooth, glabrous; at the base, densely pubescent; slightly glossy. Color: Immature involucral bracts, close to 137C and at the marginal edges, close to 145C; immature ray florets, close to 60C.

*Inflorescence diameter*.—About 2.3 cm.

*Inflorescence depth* (*height*).—About 6 cm.

*Disc diameter*.—About 1.4 cm.

*Receptacle height*.—About 5 mm.

*Receptacle diameter*.—About 7 mm.

*Receptacle shape*.—Flattened globular.

*Receptacle color*.—Close to 146D; at the center, close to 145C.

*Ray florets*.—Number of ray florets per inflorescence: About 150 arranged in about six whorls. Length: About 2.1 cm to 3.1 cm. Width: About 7.5 mm. Shape: Narrowly obovate; initially, slightly to moderately concave becoming flat with development. Apex: Obtuse. Base: Attenuate. Margin: Entire; fused at the base. Aspect: Depending on development, that is, position on receptacle, about 20 to 45 degrees from horizontal. Texture and luster, upper surface: Smooth, glabrous; slightly velvety; matte. Texture and luster, lower surface: Smooth, glabrous; slightly velvety; slightly glossy. Color: When opening, upper surface: Close to a blend of 53A and 185A. When opening, lower surface: Close to 183B; towards the margins, close to 180D. Fully opened, upper surface: Close to a blend of 181A and 185C; with subsequent development, color becoming closer to 184D and distally, closer to 22B; venation, similar to lamina colors. Fully opened, lower surface: Close to 179C and 179D flushed with close to 185D; venation, close to 185C and 185D; with subsequent development, color becoming closer to 20C and towards the center and base, flushed with close to 186C and 186D.

*Disc florets*.—Number of disc florets per inflorescence: About 100 spirally arranged at the center of the inflorescence. Length: About 7 mm. Diameter: About 2 mm. Shape: Tubular; apices acute. Texture and luster, inner surface: Smooth, glabrous; slightly velvety; slightly glossy. Texture and luster, outer surface: Smooth, glabrous; slightly velvety; glossy. Color, developing, inner and outer surfaces: Apex: Close to 14A. Mid-section: Close to 16B. Base: Close to 145C. Color, developed, inner and outer surfaces: Apex: Close to 14A. Mid-section: Close to 151D. Base: Close to 145C.

*Phyllaries*.—Number of phyllaries per inflorescence: About 30 arranged in three whorls. Length: About 8 mm. Width: About 2.5 mm. Shape: Ovate to narrowly ovate. Apex: Bluntly acute. Base: Cuneate. Margin: Entire; translucent. Texture and luster, upper surface: Smooth, glabrous; slightly glossy. Texture and luster, lower surface: Moderately pubescent; matte. Color, upper surface: Close to 143C; marginal edges, close to 145C; apex, close to 199A and 199B. Color, lower surface: Close to 137B; marginal edges, close to 154D; apex, close to 199C.

*Peduncles*.—Length, terminal peduncle: About 4.4 cm. Length, third peduncle: About 4 cm. Diameter, terminal and third peduncles: About 2 mm. Aspect, terminal peduncle: Mostly erect. Aspect, third peduncle: About 30 degrees from vertical. Strength: Strong. Texture and luster: Densely pubescent; moderately glossy. Color: Close to 146B.

*Reproductive organs*.—Androecium: Only present on disc florets. Quantity per disc floret: About five. Filament length: About 3.5 mm. Filament color: Close to 145D. Anther size: About 0.5 mm by 2 mm. Anther shape: Linear. Anther color: Close to 12A. Pollen amount: Scarce. Pollen color: Close to 15A. Gynoecium: Present on ray and disc florets. Quantity per floret: One. Pistil length: About 5 mm. Stigma diameter: About 0.2 mm. Stigma shape: Cleft, decurrent. Stigma color: Close to 16B. Style length: About 4 mm. Style color: Close to 145D. Ovary color: Close to 157A.

*Seeds and fruits*.—To date, seed and fruit production have not been observed on plants of the new *Chrysanthemum*.

Garden performance: Plants of the new *Chrysanthemum* have demonstrated good garden performance and will tolerate temperatures ranging from about −12 C to about 35 C and to be suitable for USDA Hardiness Zones 8 to 10.

Pest & pathogen resistance: Plants of the new *Chrysanthemum* have been observed to have relative resistance to Fusarium Wilt (*Fusarium oxysporum*), White Rust (*Puccinia horiana*) and Verticillium Wilt (*Verticillium alboatrum*). Plants of the new *Chrysanthemum* have not been observed to be resistant to pests and other pathogens of *Chrysanthemums*.

It is claimed:

1. A new and distinct *Chrysanthemum* plant named 'Josarrbr' as illustrated and described.

* * * * *